(12) United States Patent
Nelson et al.

(10) Patent No.: US 10,017,440 B2
(45) Date of Patent: Jul. 10, 2018

(54) METHOD FOR CONTROLLING CLEAVAGE OF HYDROPEROXIDES OF ALKYLAROMATIC HYDROCARBONS

(71) Applicant: SABIC GLOBAL TECHNOLOGIES B.V., Bergen op Zoom (NL)

(72) Inventors: Mark Erik Nelson, Mt. Vernon, IN (US); Andrey Vladimirovich Zinenkov, St. Petersburg (RU); Arkady Samuilovich Dykman, St. Petersburg (RU)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/501,188

(22) PCT Filed: Aug. 6, 2015

(86) PCT No.: PCT/IB2015/055985
§ 371 (c)(1),
(2) Date: Feb. 2, 2017

(87) PCT Pub. No.: WO2016/020879
PCT Pub. Date: Feb. 11, 2016

(65) Prior Publication Data
US 2017/0233319 A1    Aug. 17, 2017

(30) Foreign Application Priority Data
Aug. 8, 2014 (RU) ................... 2014132770

(51) Int. Cl.
| | | |
|---|---|---|
| *C08G 63/02* | (2006.01) | |
| *C07C 37/08* | (2006.01) | |
| *C08G 64/38* | (2006.01) | |
| *C07C 2/66* | (2006.01) | |
| *B01J 19/00* | (2006.01) | |
| *B01J 19/24* | (2006.01) | |
| *C07C 45/53* | (2006.01) | |
| *C07C 407/00* | (2006.01) | |

(52) U.S. Cl.
CPC ........... *C07C 37/08* (2013.01); *B01J 19/0006* (2013.01); *B01J 19/245* (2013.01); *C07C 2/66* (2013.01); *C07C 45/53* (2013.01); *C07C 407/00* (2013.01); *C08G 64/38* (2013.01); *B01J 2219/00051* (2013.01); *B01J 2219/00162* (2013.01); *B01J 2219/00164* (2013.01); *B01J 2219/24* (2013.01); *C07C 2529/06* (2013.01)

(58) Field of Classification Search
USPC ......................................... 528/196, 198, 219
See application file for complete search history.

(56) References Cited

U.S. PATENT DOCUMENTS

| | | |
|---|---|---|
| 4,329,509 A | 5/1982 | Haag et al. |
| 6,943,270 B2 | 9/2005 | Zakoshansky |
| 7,012,255 B2 | 3/2006 | Fulmer et al. |
| 7,485,758 B2 | 2/2009 | Nelson et al. |
| 8,921,610 B2 * | 12/2014 | Dakka ...................... C07C 2/74 568/385 |

FOREIGN PATENT DOCUMENTS

| | | |
|---|---|---|
| JP | 2000053641 A | 2/2000 |
| WO | 03100395 A1 | 12/2003 |

OTHER PUBLICATIONS

Written Opinion of the International Searching Authority International Application No. PCT/IB2015/055985; International Filing Date: Aug. 6, 2015; dated Nov. 26, 2015; 5 Pages.
International Search Report for International Application No. PCT/IB2015/055985; International Filing Date: Aug. 6, 2015; dated Nov. 26, 2015; 5 Pages.

* cited by examiner

*Primary Examiner* — Terressa Boykin
(74) *Attorney, Agent, or Firm* — Cantor Colburn LLP

(57) ABSTRACT

A method of producing phenol and acetone can include: alkylating benzene with a $C_{2-6}$ alkyl source in the presence of a zeolite catalyst to produce a $C_{8-12}$ alkylbenzene; oxidizing the $C_{8-12}$ alkylbenzene in the presence of an oxygen containing gas to produce a $C_{8-12}$ alkylbenzene hydroperoxide; cleaving decomposing the $C_{8-12}$ alkylbenzene hydroperoxide in the presence of an acid catalyst to produce phenol, a $C_{3-6}$ ketone, and undesirable side products such as, but not limited to acetaldehyde, DMBA, acetophenone, AMS, AMS dimers, unidentified heavies, or a combination including at least one of the foregoing; and monitoring a concentration of the $C_{8-12}$ alkylbenzene hydroperoxide in a process stream of a reactor in real time at a temperature and a pressure of the process stream; and in real time, controlling a parameter of the reactor and/or the cleaving decomposing in response to the concentration of the $C_{8-12}$ alkylbenzene hydroperoxide.

20 Claims, No Drawings

METHOD FOR CONTROLLING CLEAVAGE OF HYDROPEROXIDES OF ALKYLAROMATIC HYDROCARBONS

CROSS REFERENCE TO RELATED APPLICATIONS

This application is a 371 of International Application No. PCT/IB2015/055985, filed Aug. 6, 2015, which claims priority to Russian Application No. 2014132770, filed Aug. 8, 2014 which are incorporated herein by reference in their entirety.

BACKGROUND

A two-stage method of producing phenol and ketone can involve continuously oxidizing an alkylbenzene with oxygen to form an intermediate, an alkylbenzene hydroperoxide. For example, oxidation of the alkylbenzene cumene, also referred to as isopropylbenzene, to produce the alkylbenzene hydroperoxide cumene hydroperoxide (CHP) is shown in reaction (I).

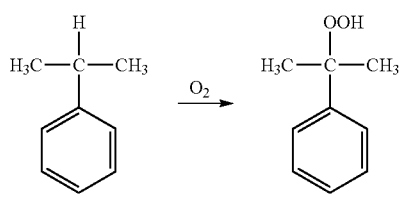

As shown in reaction (II), the intermediate CHP can then undergo acid decomposition with an acidic catalyst to form phenol and acetone. The mixture of phenol and acetone that is formed in the process can then be separated and purified such as by rectification on a distillation system.

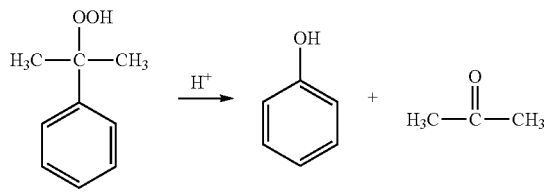

The economic efficiency of the synthesis of phenol and ketone by the alkylbenzene oxidation method can depend on attaining the highest possible yield in the two stages process of alkylbenzene oxidation and alkylbenzene hydroperoxide decomposition (also referred to as the cleavage stage). Another factor in the production of phenol and ketone by this method can be the safety of production, since both reactions, i.e., the oxidation of alkylbenzene and the decomposition of alkylbenzene hydroperoxide, are exothermic. Moreover, alkylbenzene hydroperoxides, like many other peroxide compounds, can be thermally unstable. So close monitoring of the reaction conditions and the current concentration of alkylbenzene hydroperoxide in the reaction mixture can be important to ensure the necessary level of production safety.

The oxidation of alkylbenzene can be performed in a series of reactor vessels. The yield of alkylbenzene hydroperoxide obtained during this continuous oxidation process is a function of the steady-state concentration maintained in each of the reaction vessels. To obtain a high yield of alkylbenzene hydroperoxide and provide safe working conditions, samples of the reaction mixture are routinely taken from the alkylbenzene oxidation reaction vessels. The samples can be hand-carried to the laboratory and analyzed for their alkylbenzene hydroperoxide concentration by titration methods, which can ensure the greatest accuracy and reliability. The same method of manual sampling and titration in the analytic laboratory can be used for determining the residual concentration of alkylbenzene hydroperoxide after the initial stage of its acid decomposition. Since the stage of continuous decomposition of alkylbenzene hydroperoxide can be dangerous, laboratory analyses are generally done around the clock with a frequency of about 6 to about 12 times per day, or about every 2 to about 4 hours.

Analytical laboratory methods of determining the alkylbenzene hydroperoxide content under industrial production conditions can include iodometric titration and a wet photometric method, which involves measuring the optical density after an additional reagent is added to the solution containing alkylbenzene hydroperoxide. However, both of these methods can be rather complex, can rely on the use of expensive reagents, and can be impractical for continuous industrial processes.

Another method for monitoring the alkylbenzene hydroperoxide content can include using an "on-line" industrial calorimeter analyzer. However, this method is destructive and "infers" the concentration of alkylbenzene. In this method, heat is liberated and the corresponding temperature rise is recorded. The alkylbenzene hydroperoxide concentration is then calculated from the magnitude of the temperature rise. This method can be undesirable for commercial use, since it can require a complex apparatus, can use a complex scheme of streams, and can rely on precise metering to obtain reproducible results, and can be prone to fouling of the equipment. In addition, this method can be applicable only for low concentrations of alkylbenzene hydroperoxide. Moreover, this method is not applicable for measurements in the stream at the alkylbenzene oxidation stage.

Accordingly there still remains a need in the art for a direct, non-destructive, automatic, and real time measurement process for alkylbenzene hydroperoxide concentration in industrial streams that can be used to control the manufacturing process, such as allowing for closed loop control, and in a way that can reduce the reliance on cleavage process control reagents and can optimize the production of phenol and ketone using the alkylbenzene oxidation and decomposition method.

BRIEF DESCRIPTION

Disclosed herein are methods of producing phenol and acetone.

A method of producing phenol and acetone can comprise: alkylating benzene with a $C_{2-6}$ alkyl source in the presence of a zeolite catalyst to produce a $C_{8-12}$ alkylbenzene; oxidizing the $C_{8-12}$ alkylbenzene in the presence of an oxygen containing gas to produce a C8-12 alkylbenzene hydroperoxide; cleaving decomposing the $C_{8-12}$ alkylbenzene hydroperoxide in the presence of an acid catalyst to produce phenol, an acetaldehyde, a $C_{3-6}$ ketone, and undesirable side products such as, but not limited to acetaldehyde, DMBA, acetophenone, AMS, AMS dimers, unidentified heavies or a combination comprising at least one of the foregoing; and monitoring a concentration of the $C_{8-12}$ alkylbenzene hydroperoxide in a process stream of a reactor in real time at a temperature and a pressure of the process stream; and in real time, controlling a parameter of the reactor and/or the cleaving decomposing in response to the concentration of the $C_{8-12}$ alkylbenzene hydroperoxide.

A method of producing phenol and acetone from a $C_{8-12}$ alkylbenzene hydroperoxide in a process stream of a reactor can comprise: immersing a portion of a probe coupled to a spectrometer into the process stream comprising a flow direction, a temperature, and a pressure; monitoring absorption data with the spectrometer in the range from 900 nm to 2500 nm in real time; calculating a concentration of the $C_{8-12}$ alkylbenzene hydroperoxide in the reaction stream from the absorption data, and controlling a parameter of the reactor or the reaction stream in response to the calculated concentration.

A reactor can comprise: a reaction vessel comprising an inlet conduit directing an inlet stream, an outlet conduit directing an outlet stream; a probe inserted into one of the inlet conduit, the reaction vessel, and the outlet conduit, wherein the probe is coupled to a spectrometer and is configured to measure the concentration of a $C_{8-12}$ alkylbenzene hydroperoxide, a di($C_{8-12}$ alkylbenzyl) peroxide, water, acetone, phenol, hydroperoxide, dimethylbenzyl alcohol, acetaldehyde, a $C_{3-6}$ ketone, a $C_{8-12}$ alkylbenzene, α-methylstyrene, or a combination comprising at least one of the foregoing; and a distributed control system in electrical communication with the probe and a control device, wherein the control device is configured to control a flow rate of the inlet stream, a temperature of the inlet stream, a pressure of the inlet stream, the temperature of the reaction vessel, the pressure of the reaction vessel, or a combination comprising at least one of the foregoing.

The above described and other features are exemplified by the following detailed description.

DETAILED DESCRIPTION

The production of a phenol and a ketone can include the oxidation of an alkylbenzene to form an alkylbenzene hydroperoxide and decomposition of the alkylbenzene hydroperoxide. The oxidation and decomposition reactions can include side reactions that can reduce the yield of the desired product of the reactions (e.g., alkylbenzene hydroperoxide, benzyl alcohol, and ketone). To maximize product yield it can be desirable to reduce or eliminate the occurrence of these side reactions. To reduce the production cost it can be desirable to reduce or eliminate reagents, process steps, manual operations, or a combination including at least one of the foregoing.

In the decomposition stage, an alkylbenzene hydroperoxide can be decomposed to phenol and a ketone. The decomposition reaction is exothermic. The decomposition reaction can include a catalyst such as a protic acid (e.g. $H_2SO_4$). The extent of the decomposition can depend on the amount of protic acid in the reacting mixture. Increased protic acid concentration can result in a corresponding increase in the temperature of the reactor (e.g., the temperature of the reaction mixture) as the amount of alkylbenzene peroxide that decomposes to form phenol and a ketone product increases and a corresponding amount of heat is released into the reaction mixture.

To limit the temperature and/or extent of reaction within a reactor the amount of the protic acid that is available to react can be controlled. A strategy to control the extent of reaction in a reactor can include adjusting the flow rate of the protic acid into the reactor. Another strategy can include providing a catalyst activity balancing system which can adjust parameters of the reaction mixture to achieve a desired conversion, temperature, species concentration, or a combination including at least one of the foregoing. A catalyst activity balancing system can include an acid suppressing agent which can be added to the reaction mixture. An acid suppressing agent can include an alkaline reagent (e.g., ammonia), a solvent (e.g., water, a ketone, such as acetone, and the like), or a combination of at least one of the foregoing. Another strategy can include controlling the extent of reaction in a reactor by controlling the reaction mixture temperature. For example the temperature of a reaction mixture in a reactor can be controlled by adjusting the coolant flow rate and/or temperature set point of the coolant supplied to the decomposition reactor such that the temperature of the reaction mixture is maintained from 35° C. to 95° C., for example, 40° C. to 75° C., or 45° C. to 65° C. The concentration of hydroperoxides of an alkylbenzene in liquid industrial streams can be measured at any stage of a process directly using a spectroscopic method. The spectrometer employed in the spectroscopic method can be calibrated according to a series of known concentrations of the hydroperoxide solutions, which correspond to a desired range of concentrations that are to be measured. A calibration model obtained from the known concentrations can be stored in the memory of a computer by appropriate software. Analysis of a sample for its hydroperoxide content can then be carried out directly in the stream. The spectroscopic method can include measurement in the near infrared spectrum, with the concentration of hydroperoxide in the stream being calculated using the calibration model. Measuring the concentration of a reaction product can improve control of the production process, reduce the time and labor expended in analysis, and also to increase the safety level and decrease the cost of production. Continual monitoring of the product stream and adjusting a parameter of the reactor or process (e.g., flow rate of the reactor input stream(s), reactor temperature, reactor pressure and the like) can lead to a more efficient process and can reduce and/or eliminate the need for subsequent reagents (e.g., ammonia, acid catalyst) to achieve optimal reactor conditions (e.g., reactant conversion, product yield). These control techniques can include closed loop control where a parameter of the reactor is controlled based on feedback from the process such as a measured output variable of the reactor. These control techniques can include open loop control where a parameter of the reactor is controlled without feedback from the process.

The control method can be based on direct measurement of the concentration of hydroperoxides in liquid industrial streams and feedback of this measurement into the control of the process inputs to achieve a target hydroperoxide concentration. A controller can be used to drive the difference between a desired value for a process parameter (e.g., process output such as CHP concentration setpoint) and a measured parameter to zero. The controller can use any suitable control algorithm to drive this difference (also referred to as "error") between the setpoint and the measured parameter to zero. For example, the algorithm can include proportional error, integral error, differential error, or a combination including at least one of the foregoing, as in, for example, a proportional-integral-differential (PID) control algorithm. The controller can use any type of control techniques, including, for example, logic sequencing, neural networks, Bayesian probability, fuzzy logic, machine learning, and evolutionary computation. Alternatively, control system can be manually controlled based on the measured parameter.

A control system can include a measurement device such as a NIR spectrometer, a computer in electronic communication with the measurement device, and a controller which can adjust a parameter of the reactor (e.g., a distributed control system element such as a mass flow controller, heater, pump, and the like). The computer can include a chemometric model stored in its memory for comparison to a signal obtained from the measurement device.

A parameter of the process or reactor can include a temperature of the reactor, a temperature of a process stream, a pressure of the process stream, a pressure of the reactor, a flow rate of the process stream (e.g., any process stream, such as a reactor input stream, an acid neutralizer stream, a recycle stream, and the like), a concentration of an alkylbenzene hydroperoxide, a concentration of a cleavage catalyst, a concentration of a species in the reactor (e.g., the concentration of alkylbenzene, the concentration of water, a concentration of ammonia, or a combination including at least one of the foregoing.

The measurement method can be spectroscopic. The measurement method can include measuring the absorption of near infrared spectrum wavelengths of electromagnetic radiation. As used herein, the term near infrared (NIR) can include a range of electromagnetic radiation wavelengths of 770 to 2,500 nanometer (nm) in air (e.g., a frequency range of 390 TeraHertz (THz) to 119 THz), for example, 900 nm to 2,500 nm in air (e.g., a frequency of 333 THz to 119 THz), or 1,100 nm to 2,200 nm in air (e.g., a frequency of 272 THz to 136 THz). The measurement method is non-destructive.

The measurement method can make it possible to obtain values of the concentration of hydroperoxides in the process stream automatically, continuously, and in "real time". The interval between subsequent measurements can be less than or equal to 1 second, for example, the interval can be 0.1 to 0.5 second, or, 0.1 to 0.2 second. Accordingly the sample rate of the measurement method can be greater than or equal to 1 sample per second, for example, 2 to 10 samples per second, or, 5 to 10 samples per second.

Suitable spectrometers can include scanning spectrometers, with a Fourier transform, with sets of filters, Raman spectrometers, and the like. Other suitable spectrometers will be apparent to those skilled in the art in view of this disclosure.

A spectrometer probe can be made of an inert material, for example, a non-reactive metal (e.g., stainless steel), ceramic, plastics (e.g., polytetrafluoroethylene (PTFE)), fiber optic material, and the like. A probe can be placed directly into a process stream of a production system (e.g., including a reaction process, flow equipment and the like). The probe can be disposed at any point of the production system. The probe can be located in an analysis port (e.g., port, fitting, or similar pass through into a conduit, reactor, vessel, or the like) at any location along a reaction process system for direct measurement of a process variable. The probe can be placed directly into a sample taken from a process stream of a production system. The probe can be employed in a laboratory setting.

A phenol and ketone production system can include multiple reactors. Reactors of the production system can have a serial arrangement where the output of a first reactor provides an input to a second reactor, and the output of the second reactor provides an input to a third reactor and so forth. The serial arrangement can repeat for any number of reactors. The production system can include a recycle stream, where the output of a vessel is returned to an upstream section of the process for subsequent processing. The cleavage process can include a single stage, such as in a boiling cleavage process, and a single monitoring probe can be located at the exit of the single cleavage stage. The production system can include a two stage alkylbenzene hydroperoxide cleavage process. In a two stage cleavage process, a single monitoring probe can be used where it can be located at the exit of the first stage or at the exit of the second stage. In a two stage cleavage process, two or more monitoring probes can be used where a first probe is located at the exit of the first stage and a second probe is located at the exit of the second stage. In this case, the first probe can be used to control the conversion of an intermediate species (e.g., dimethylbenzyl alcohol (DMBA) and to dicumyl peroxide (DCP)) such as in a cumene conversion process and the second probe can be used to control the decomposition of dicumylperoxide to phenol, $\alpha$-methyl styrene (AMS), and a ketone. The probe can be used to optimize the reaction products from a single reactor vessel. The probe can be used to monitor the feed composition to a reactor (e.g., a first reactor a first cleavage stage). The probe can be used to control the feed composition of a stream of a reactor (e.g., a first reactor a first cleavage stage). A first stage of a two stage cleavage process can include one or more reactors (e.g. three serially arranged reactors). In this case, a probe can be located at the exit and/or entrance of each of the one or more reactors to monitor and/or control the concentration of the species at each location.

The probe can be sensitive to the orientation of the optical path relative to the direction of flow of the fluid stream that is being measured by the probe. The probe can be oriented in a process stream so as to avoid the possibility of cavitation of the process fluid adjacent to the probe. For example, to avoid cavitation, the probe can be oriented such that the optical path of the probe can be at an angle of 85° to 95° relative to the direction of flow crossing the optical path.

The probe can be connected to the spectrometer using fiber-optic cables or the like. When the spectrometer probe is put in the sample (including a conduit carrying a process stream), the concentration of species within the stream (e.g. alkylbenzene hydroperoxide) can be measured by reading the spectrum and using the corresponding calibration of the device. Special software for the NIR spectrometer can calculate the species concentrations from the signal that is measured. The NIR spectrometer, the fiber-optic probes, and the equipment connected with them can be free of moving parts (or can include few of them), which can reduce service cost and can improve reliability in comparison to monitoring systems that rely on moving parts (e.g., sampling pumps such as in calorimetric methods that require reagent addition).

The NIR spectrometer can rely on accurate calibration. The calibration of the NIR spectrometer can be performed with standard solutions containing known concentrations of the species of the reaction process. The calibration model can be stable over a long period of time. The standard software for the NIR spectrometer can perform the required calculations on one wavelength at which the absorption can be quantitatively connected with an alkylbenzene hydroperoxide concentration in accordance with the Bouguer-Lambert-Beer law. Measurements at a single wavelength are possible; however, it can be desirable to use more complex chemometric models. These models can be built on two or more wavelengths and can provide better accuracy and reproducibility. These models can use two or more wavelengths, for example, no fewer than the number of components desired in the analytical model, which are selected from the NIR spectrum. A calculation algorithm can use a multiple linear regression (MLR) method, Principle Component Regression (PCR), or a method of partial least squares (PLS). These chemometric models can be built on two or more wavelengths and over a range of temperatures to improve their accuracy. Incorporating temperature compensation into the chemometric model can improve the accuracy of the "real time" measurement which can be done in a process stream at process temperature. A chemometric model can include NIR absorption data as a function of temperature for one or more species of the process. The NIR absorption data can be taken at more than two temperatures, for example, 2 to 100, or 2 to 50 temperatures which can improve the accuracy of the measurement and corresponding control. The accuracy of the NIR measurements can be improved by maintaining a thermostatic condition at the sample location such as with a temperature controller. An important factor in selecting the algorithm can be its ability to exclude absorption bands from other components that are present in the mixture, such as an alkylbenzene, a benzyl alcohol, a ketone, or the like, from the calculation as these absorption bands can be superimposed on those of an alkylbenzene hydroperoxide.

Automatic "on-line" continuous determination of CHP in the commercial process stream at the stages of alkylbenzene oxidation and alkylbenzene hydroperoxide decomposition can make it possible to conduct the process in a safer way compared to the other control methods and can have a significant economic effect by giving greater operative control over the process, especially if the data are used immediately in "real time" to control the reactor system. In this case, the controller can use the digital data from the analyzer to adjust the process inputs (e.g., reactor temperature, reactor pressure, reactant flow rate, reactant concentration, and the like) which can optimize the process, such as to achieve maximum yield and the greatest safety.

Controlling the production of phenol and ketone by monitoring the reaction process using NIR spectroscopy and correspondingly controlling a process parameter can reduce or eliminate the need for an alkaline reagent to counteract an acidic decomposition catalyst. Such control methods can allow for an ammonia free process, whereby 0 weight percent (wt. %) ammonia is present in a decomposition reactor.

An alkylbenzene can include any alkylbenzene, for example, a $C_{8-12}$ alkylbenzene such as isopropylbenzene (cumene), sec-butylbenzene, diisopropylbenzene, or a combination including at least one of the foregoing. A benzyl alcohol can include any benzyl alcohol, for example, a $C_{6-10}$ benzyl alcohol, such as phenol,1,3-dioxybenzene (resorcinol), 1,4-dioxy benzene (hydroquinone), 1,2-dioxy benzene, cresols, alkyl phenols, or a combination including at least one of the foregoing. A ketone can include any ketone, for example, an aromatic ketone such as acetophenone, or a $C_{3-6}$ ketone such as acetone, methyl ethyl ketone (MEK or butanone), pentanone, hexanone, cyclohexanone, or a combination including at least one of the foregoing.

The measurement method can be used at the alkylbenzene oxidation stage, at the alkylbenzene hydroperoxide decomposition stage, or at both stages. The composition of samples and the species of the reaction mixture can differ at each stage and at the specific sample location. For example, the products of cumene oxidation can include, in addition to cumene hydroperoxide (CHP) and cumene, which can be present in large concentrations, components such as acetophenone, 2-phenyl-2-propanol (dimethylbenzyl alcohol, DMBA), and water, while the concentration of CHP in the CHP decomposition reaction mixture can be much lower and the basic components of this mixture can include cumene, acetone, and phenol. Nevertheless, the CHP concentration can be analyzed quickly and precisely.

Advantages of real time NIR spectrometric monitoring and control of the production process can include providing non-destructive measurement of the concentration of alkylbenzene hydroperoxide, which can save time, labor, and reagent expenses; allowing for rapid measurement of the process stream or vessel concentration at areas in the process where safety risk can be high (e.g., hydroperoxide formation, hydroperoxide pumping, and the like); providing measurement which can be used by the process control system to increase process efficiency and reduce operational costs; and eliminating delay resulting from off-line laboratory measurement methods. Another advantage of real time NIR analysis is the conversion of discrete compositional data to a continuous data function allowing process optimization based on composition as well as conventional process parameters such as temperature, pressure, and flow.

EXAMPLES

CHP decomposition process control experiments were performed using a specially designed pilot installation which simulated a phenol and acetone production process. The pilot installation used a two-stage CHP decomposition process to produce phenol and acetone. The first stage included a series of three reactors, and a circulation loop returning a portion of the product effluent to the inlet of first reactor together with a CHP decomposition feed. The balance of first stage decomposition product (the portion not recirculated) was passed through a second decomposition stage including a plug flow reactor which provided complete CHP decomposition into phenol and acetone as well as nearly complete decomposition of DCP (which was formed in the first stage reactors from CHP and DMBA).

On-line analysis of CHP decomposition process streams was conducted by installing flow cells into the pilot installation at the CHP feed (upstream of the recycle), at the exit of the first reactor of the first stage (R1.1), at the exit of the second reactor of the first stage (R1.2), at the exit of the third reactor of the first stage (R1.3), and at the exit of the reactor second stage. The flow cells were used to obtain spectra in real time during operation of the pilot installation. Each flow cell which was installed had a 10 mm optical path process interface and fiber optic spectral instrument interface. A Guided Wave Model 412 XNIR spectrophotometer was used for data collection. The spectrophotometer sampled the spectra of the reaction mixture at a rate of less than 6 seconds per channel, and less than 30 seconds for all channel data. Species concentrations were calculated with a calibrated chemometric model in less than 1 second after the spectra was sampled and was used to control the decomposition process.

The calibrated chemometric model was prepared by obtaining spectral data of reference samples, having known concentration of species of interest, using the Unscrambler™ software (commercially available from Camo Inc.). The species of interest included in the calibration data set included CHP, DCP, DMBA, AMS, cumene, phenol, acetone, water, and acetophenone. The calibration data set used for the pilot installation control contained 138 samples covering the extended concentration ranges present in the process. Calibration error for the reaction mixture components is presented in Table 1. The sample spectra were recorded for temperatures of 20° C. to 60° C. to provide a temperature-compensated calibration.

TABLE 1

CHP cleavage product NIR online analysis calibration error

| Component | Maximal concentration, wt. % | Calibration error, wt. % |
|---|---|---|
| CHP | 6 | 0.1 |
| DCP | 8 | 0.4 |
| Phenol | 60 | 0.3 |
| Acetone | 50 | 0.2 |
| AMS | 4 | 0.06 |
| DMBA | 4.5 | 0.03 |
| Cumene | 6 | 0.03 |
| Acetophenone | 1.5 | 0.12 |
| Water | 2.5 | 0.02 |

The startup process of the CHP decomposition pilot installation included filling the system with a phenol-acetone mixture having catalyst concentration of 150% to 200% of the normal operational concentration of catalyst in the system (before the CHP feed was started to avoid excessive CHP concentration in the reactor system which can result in overheating the coolant system as the decomposition takes place), heating the reactors to the normal operating temperature, and feeding CHP and catalyst at the normal operational rate.

Following this procedure the CHP decomposition system achieved stead state operation in approximately 4 hours according to spectral data obtained. After this time the time-based variation of the concentration of each specie in the reaction mixture was less than the measurement-to-measurement error of the NIR spectrophotometer.

Online measurement of CHP and DCP concentrations provided the opportunity to safely accelerate the startup process since a direct measurement of key components was possible. As a result, the catalyst could be introduced at a lower rate in comparison to before online spectral analysis was implemented.

The accelerated startup process of the CHP decomposition pilot installation included filling the system with phenol-acetone mixture having a catalyst concentration 100% to 120% of normal operational concentration of catalyst in the system, heating the reactors to the normal operating temperature, feeding CHP and catalyst at the normal operational rate, adjusting (e.g., continuously) the catalyst flow rate to provide the desired CHP concentration (or conversion) which can correspond to the optimal process conditions for a particular feed composition (e.g., maintaining a range 0.5% to 1% CHP in the reaction mixture at the exit of the first cleavage stage, at location R1.3, providing complete CHP and DCP conversion after the second cleavage stage, at location R2, and controlling the CHP concentration with a process control system. Following this procedure the CHP decomposition system achieved stead state operation in approximately 1 hour according to spectral data obtained.

Additionally, with the continuous online monitoring the process control system was able to detect a high CHP concentration, symptomatic of low catalyst feed rate (e.g., a catalyst feed pump fault) in less than 5 minutes. The process control system was then able to automatically initiate corrective action including feeding an alkali agent (e.g., sodium phenate, sodium carbonate) into the reaction mixture to cease the decomposition reaction and/or stopping the CHP feed to prevent buildup of CHP concentration within the system.

Embodiment 1: A method of producing phenol and acetone comprising: alkylating benzene with a $C_{2-6}$ alkyl source in the presence of a zeolite catalyst to produce a $C_{8-12}$ alkylbenzene; oxidizing the $C_{8-12}$ alkylbenzene in the presence of an oxygen containing gas to produce a $C_{8-12}$ alkylbenzene hydroperoxide; decomposing the $C_{8-12}$ alkylbenzene hydroperoxide in the presence of an acid catalyst to produce phenol, a $C_{3-6}$ ketone, or a combination comprising at least one of the foregoing; and monitoring a concentration of the $C_{8-12}$ alkylbenzene hydroperoxide in a process stream of a reactor in real time at a temperature and a pressure of the process stream; and in real time, controlling a parameter of the reactor and/or the decomposing in response to the concentration of the $C_{8-12}$ alkylbenzene hydroperoxide.

Embodiment 2: The method of Embodiment 1, wherein decomposing is ammonia free.

Embodiment 3: The method of any of Embodiments 1-2, wherein the monitoring occurs before decomposing the $C_{8-12}$ alkylbenzene hydroperoxide, after decomposing the $C_{8-12}$ alkylbenzene hydroperoxide, or both before and after decomposing the $C_{8-12}$ alkylbenzene hydroperoxide.

Embodiment 4: The method of any of Embodiments 1-3, wherein the monitoring comprises using a near infrared probe located downstream of at least a portion of the decomposing.

Embodiment 5: The method of any of Embodiments 1-4, wherein monitoring further comprises immersing a portion of a probe coupled to a spectrometer into the process stream having a flow direction; and further comprising orienting the probe to an angle of 85 degrees to 95 degrees relative to a plane that is perpendicular to the flow direction.

Embodiment 6: The method of any of Embodiments 1-5, wherein monitoring further comprises collecting absorption data of the process stream with the spectrometer in the range from 900 nm to 2500 nm.

Embodiment 7: A method of producing phenol and acetone from a $C_{8-12}$ alkylbenzene hydroperoxide in a process stream of a reactor, the method comprising: immersing a portion of a probe coupled to a spectrometer into the process stream comprising a flow direction, a temperature, and a pressure; monitoring absorption data with the spectrometer in the range from 900 nm to 2500 nm in real time; calculating a concentration of the $C_{8-12}$ alkylbenzene hydroperoxide in the reaction stream from the absorption data, and controlling a parameter of the reactor or the reaction stream in response to the calculated concentration.

Embodiment 8: The method of Embodiment 7, further comprising orienting the probe to an angle of 85 degrees to 95 degrees relative to a plane that is perpendicular to the flow direction.

Embodiment 9: The method of any of Embodiments 5-8, wherein the spectrometer is a near infrared analyzer.

Embodiment 10: The method of any of Embodiments 6-9, wherein the monitoring of absorption data is in the range from 1100 to 2200 nm.

Embodiment 11: The method of any of Embodiments 1-10, wherein the monitoring occurs continuously.

Embodiment 12: The method of any of Embodiments 1-11, wherein the monitoring in real time comprises sampling at a sample rate of greater than or equal to 1 sample per minute.

Embodiment 13: The method of any of Embodiments 1-12, further comprising adjusting the catalyst activity in the process stream. Optionally, the catalyst activity can be adjusted by adjusting the pH of the process stream.

Embodiment 14: The method of Embodiment 13, wherein adjusting the catalyst activity consists of adjusting an inlet flow rate to the reactor of water, acetone, acid catalyst, or a combination comprising at least one of the foregoing.

Embodiment 15: The method of any of Embodiments 1-14, comprising adding 0 wt. % of an alkaline pH balancing reagent to the reactor.

Embodiment 16: The method of any of Embodiments 1-15, comprising adding 0 wt. % ammonia to the reactor.

Embodiment 17: The method of any of Embodiments 5-16, further comprising locating the probe in the reactor at a location comprising before a decomposition reactor, after the decomposition reactor, in a sample line of the process stream, in a main line of the process stream, in a sample cell, or a combination comprising at least one of the foregoing.

Embodiment 18: The method of any of Embodiments 1-17, wherein the parameter is a temperature of the reactor, a temperature of the process stream, a pressure of the process stream, a flow rate of the process stream, the concentration of the $C_{8-12}$ alkylbenzene hydroperoxide, a concentration of the cleavage catalyst, a concentration of an oxidation catalyst, a concentration of the $C_{8-12}$ alkylbenzene, a concentration of water, a concentration of ammonia, a pressure of the reactor, or a combination of at least one of the foregoing.

Embodiment 19: The method of any of Embodiments 1-18, wherein the parameter is a concentration of water and wherein the concentration of water is controlled such that a temperature of the reaction mixture is maintained from 45° C. and 65° C.

Embodiment 20: The method of any of Embodiments 1-19, wherein the controlling the parameter of the reactor comprises comparing the concentration to a chemometric model, and wherein the chemometric model had been formed by monitoring concentration using ultra-pressure liquid chromatography.

Embodiment 21: The method of any of Embodiments 1-20, further comprising developing a temperature compensating chemometric model; and controlling the parameter of the reactor further comprises comparing the concentration of the $C_{8-12}$ alkylbenzene hydroperoxide to the temperature compensating chemometric model.

Embodiment 22: The method of Embodiment 21, wherein developing a temperature compensating chemometric model further comprises analyzing a chemical composition of the process stream at multiple temperatures.

Embodiment 23: The method of any of Embodiments 1-22, further comprising monitoring the concentration of di($C_{8-12}$ alkylbenzyl) peroxide, water, acetone, phenol, hydroperoxide, dimethylbenzyl alcohol, acetone, $C_{8-12}$ alkylbenzene, α-methylstyrene or a combination comprising at least one of the foregoing.

Embodiment 24: The method of any of Embodiments 1-23, comprising achieving a conversion of dimethylbenzyl alcohol to α-methylstyrene in the process stream of the reactor of greater than or equal to 80%.

Embodiment 25: The method of any of Embodiments 1-24, comprising converting the $C_{8-12}$ alkylbenzene hydroperoxide in the absence of ammonia.

Embodiment 26: The method of Embodiment 1, wherein the oxygen containing gas comprises air.

Embodiment 27: The use of the phenol produced by the method of any of Embodiments 1-26 to produce bisphenol A.

Embodiment 28: A method for the manufacture of bisphenol A, comprising reacting the phenol and/or acetone produced by the method of any of Embodiments 1-27 in the presence of a catalyst to form bisphenol A.

Embodiment 29: The use of the bisphenol A of any of Embodiments 27-28 to produce polycarbonate.

Embodiment 30: A process for the production of polycarbonate, comprising contacting the bisphenol A of any of Embodiments 27-28 with a carbonyl source in the presence of a catalyst and under polycarbonate-forming conditions, to produce the polycarbonate.

Embodiment 31: A polycarbonate produced by the process of Embodiment 30.

Embodiment 32: A reactor comprising: a reaction vessel comprising an inlet conduit directing an inlet stream, an outlet conduit directing an outlet stream; a probe inserted into one of the inlet conduit, the reaction vessel, and the outlet conduit, wherein the probe is coupled to a spectrometer and is configured to measure the concentration of a $C_{8-12}$ alkylbenzene hydroperoxide, a di($C_{8-12}$ alkylbenzyl) peroxide, water, acetone, phenol, hydroperoxide, dimethylbenzyl alcohol, acetaldehyde, a $C_{3-6}$ ketone, a $C_{8-12}$ alkylbenzene, α-methylstyrene, or a combination comprising at least one of the foregoing; and a distributed control system in electrical communication with the probe and a control device, wherein the control device is configured to control a flow rate of the inlet stream, a temperature of the inlet stream, a pressure of the inlet stream, the temperature of the reaction vessel, the pressure of the reaction vessel, or a combination comprising at least one of the foregoing.

Embodiment 33: The reactor of Embodiment 32, comprising two or more reaction vessels where the reaction vessels are connected in fluid communication in a serial flow arrangement and wherein the probe is located in the outlet conduit downstream of a last reaction vessel.

Embodiment 34: The reactor of any of Embodiments 32-33, comprising three reaction vessels, and wherein the reaction vessels are connected in fluid communication in a serial flow arrangement and wherein the probe is located in the outlet conduit downstream of a last reaction vessel.

Embodiment 35: The reactor of any of Embodiments 32-34, wherein the spectrometer is a near infrared analyzer.

Embodiment 36: The reactor of any of Embodiments 32-35, wherein the spectrometer is configured to measure absorption data in the range from 900 nm to 2500 nm in real time.

Embodiment 37: The reactor of any of Embodiments 32-36, wherein the probe is oriented such that an optical path of the probe is crossed by the process stream at an angle of 85 degrees to 95 degrees.

Embodiment 38: The reactor of any of Embodiments 32-37, wherein the reactor is capable of achieving a conversion of the dimethylbenzyl alcohol to α-methylstyrene of greater than or equal to 80%.

Embodiment 39: The reactor of any of Embodiments 32-38, further comprising a catalyst activity balancing system for adjusting the catalytic activity of a reaction mixture, and wherein the catalyst activity balancing system is free of ammonia. Optionally, the catalyst activity can be adjusted by adjusting the pH of the process stream Embodiment 40: The reactor of any of Embodiments 32-39, wherein the probe is retractable.

Embodiment 41: The method of any of Embodiments 1-28, wherein the oxidizing can further produce undesirable side products including acetaldehyde, DMBA, acetophenone, AMS, AMS dimers, as well as combinations comprising at least one of the foregoing. It can even produce unidentified heavies and other undesirable side products.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

All ranges disclosed herein are inclusive of the endpoints, and the endpoints are independently combinable with each other (e.g., ranges of "up to 25 wt. % or, more specifically, 5 wt. % to 20 wt. %", is inclusive of the endpoints and all intermediate values of the ranges of "5 wt. % to 25 wt. %," etc.). "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

We claim:

1. A method of producing phenol and a $C_{3-6}$ ketone, comprising:
    alkylating benzene with a $C_{2-6}$ alkyl source in the presence of a zeolite catalyst to produce a $C_{8-12}$ alkylbenzene;
    oxidizing the $C_{8-12}$ alkylbenzene in the presence of an oxygen containing gas to produce a $C_{8-12}$ alkylbenzene hydroperoxide;
    decomposing the $C_{8-12}$ alkylbenzene hydroperoxide in the presence of an acid catalyst to produce phenol, a $C_{3-6}$ ketone, or a combination comprising at least one of the foregoing;
    monitoring a concentration of the $C_{8-12}$ alkylbenzene hydroperoxide in a process stream of a reactor in real time at a temperature and a pressure of the process stream; and
    in real time, controlling a parameter of the reactor and/or the decomposing in response to the concentration of the $C_{8-12}$ alkylbenzene hydroperoxide, wherein the parameter is a flow rate of the process stream, a pressure of the process stream, a pressure of the reactor, the concentration of the $C_{8-12}$ alkylbenzene hydroperoxide, a concentration of the cleavage catalyst, a concentration of an oxidation catalyst, a concentration of the $C_{8-12}$ alkylbenzene, a concentration of water, a concentration of ammonia, or a combination of at least one of the foregoing.

2. The method of claim 1, wherein decomposing is ammonia free.

3. The method of claim 1, wherein the monitoring occurs before decomposing the $C_{8-12}$ alkylbenzene hydroperoxide, after decomposing the $C_{8-12}$ alkylbenzene hydroperoxide, or both before and after decomposing the $C_{8-12}$ alkylbenzene hydroperoxide.

4. The method of any of claim 1, wherein the monitoring comprises using a near infrared probe located downstream of at least a portion of the decomposing.

5. The method of claim 1, wherein monitoring further comprises immersing a portion of a probe coupled to a spectrometer into the process stream having a flow direction; and further comprising orienting an optical path of the probe to an angle of 85 degrees to 95 degrees relative to the flow direction.

6. A method of producing phenol and a $C_{3-6}$ ketone from a $C_{8-12}$ alkylbenzene hydroperoxide in a process stream of a reactor, the method comprising:
    immersing a portion of a probe coupled to a spectrometer into the process stream comprising a flow direction, a temperature, and a pressure;
    monitoring absorption data with the spectrometer in the range from 900 nm to 2500 nm in real time;
    calculating a concentration of the $C_{8-12}$ alkylbenzene hydroperoxide in the reaction stream from the absorption data, and
    controlling a parameter of the reactor or the reaction stream in response to the calculated concentration, wherein the parameter is a flow rate of the process stream, a pressure of the process stream, a pressure of the reactor, the concentration of the $C_{8-12}$ alkylbenzene hydroperoxide, a concentration of the cleavage catalyst, a concentration of an oxidation catalyst, a concentration of the $C_{8-12}$ alkylbenzene, a concentration of water, a concentration of ammonia, or a combination of at least one of the foregoing.

7. The method of claim 6, wherein the monitoring of absorption data is in the range from 1100 to 2200 nm.

8. The method of claim 1, wherein the monitoring in real time comprises sampling at a sample rate of greater than or equal to 1 sample per minute.

9. The method of claim 1, further comprising adjusting the catalyst activity in the process stream; wherein adjusting the catalyst activity consists of adjusting an inlet flow rate to the reactor of water, acetone, acid catalyst, or a combination comprising at least one of the foregoing.

10. The method of claim 1, wherein the parameter is a concentration of water and wherein the concentration of water is controlled such that a temperature of the reaction mixture is maintained from 45° C. and 65° C.

11. The method of claim 1, wherein the controlling the parameter of the reactor comprises comparing the concentration to a chemometric model, and wherein the chemometric model had been formed by monitoring concentration using ultra-pressure liquid chromatography.

12. The method of claim 1, further comprising developing a temperature compensating chemometric model; and controlling the parameter of the reactor further comprises comparing the concentration of the $C_{8-12}$ alkylbenzene hydroperoxide to the temperature compensating chemometric model.

13. The method of claim 1, further comprising monitoring the concentration of di($C_{8-12}$ alkylbenzyl) peroxide, water, acetone, phenol, hydroperoxide, dimethylbenzyl alcohol, $C_{8-12}$ alkylbenzene, α-methylstyrene or a combination comprising at least one of the foregoing.

14. A method for the manufacture of bisphenol A, comprising reacting the phenol and/or $C_{3-6}$ ketone produced by the method of claim 1 in the presence of a catalyst to form bisphenol A.

15. A process for the production of polycarbonate, comprising contacting the bisphenol A of claim 14 with a carbonyl source in the presence of a catalyst and under polycarbonate-forming conditions, to produce the polycarbonate.

16. A reactor comprising:
a reaction vessel comprising an inlet conduit directing an inlet stream, an outlet conduit directing an outlet stream;
a probe inserted into one of the inlet conduit, the reaction vessel, and the outlet conduit, wherein the probe is coupled to a spectrometer and is configured to measure the concentration of a $C_{8-12}$ alkylbenzene hydroperoxide, a di($C_{8-12}$ alkylbenzyl) peroxide, water, acetone, phenol, hydroperoxide, dimethylbenzyl alcohol, acetaldehyde, a $C_{3-6}$ ketone, a $C_{8-12}$ alkylbenzene, α-methylstyrene, or a combination comprising at least one of the foregoing; and
a distributed control system in electrical communication with the probe and a control device, wherein the control device is configured to control a flow rate of the inlet stream, a temperature of the inlet stream, a pressure of the inlet stream, the temperature of the reaction vessel, the pressure of the reaction vessel, or a combination comprising at least one of the foregoing.

17. The reactor of claim 16, comprising two or more reaction vessels where the reaction vessels are connected in fluid communication in a serial flow arrangement and wherein the probe is located in the outlet conduit downstream of a last reaction vessel.

18. The reactor of claim 16, wherein the reactor is capable of achieving a conversion of the dimethylbenzyl alcohol to α-methylstyrene of greater than or equal to 80%.

19. The reactor of claim 16, further comprising a catalyst activity balancing system for adjusting the catalytic activity of a reaction mixture, and wherein the catalyst activity balancing system is free of ammonia.

20. The reactor of claim 16, wherein the probe is retractable.

* * * * *